United States Patent [19]

Bennoit et al.

[11] Patent Number: 4,851,134
[45] Date of Patent: Jul. 25, 1989

[54] PROCESS AND APPARATUS FOR THE REMOVAL OF SOLID PARTICLES FROM LIQUID CHLORINATED HYDROCARBONS

[75] Inventors: Horst Bennoit, Völklingen; Walter Fröhlich, Burgkirchen; Rolf Höltermann, Neuötting; Reinhard Krumböck, Burgkirchen, all of Fed. Rep. of Germany

[73] Assignee: Hoechst Aktiengesellschaft, Fed. Rep. of Germany

[21] Appl. No.: 166,092

[22] Filed: Mar. 9, 1988

[30] Foreign Application Priority Data

Mar. 12, 1987 [DE] Fed. Rep. of Germany ....... 3708010

[51] Int. Cl.⁴ .......................................... B01D 17/038
[52] U.S. Cl. ..................................... 210/788; 570/222
[58] Field of Search ............... 570/227, 219; 210/787, 210/788, 512.1, 512.2; 209/144, 211

[56] References Cited

U.S. PATENT DOCUMENTS

| 3,879,482 | 4/1975 | Riegel | 570/222 |
| 3,919,336 | 11/1975 | Kurtz | 570/219 |
| 3,937,744 | 2/1976 | Riegel | 570/222 |

FOREIGN PATENT DOCUMENTS 3219352 11/1983 Fed. Rep. of Germany .

Primary Examiner—Frank Sever
Attorney, Agent, or Firm—Connolly and Hutz

[57] ABSTRACT

A process for the removal of solid particles from a mixture containing at least one liquid chlorinated hydrocarbon is described. The solids-containing liquid mixture is introduced into at least one hydrocyclone having a downstream separator. The liquid mixture which has been enriched in solids and discharged from the hydrocyclone is preferably subjected to sedimentation of the solid particles, without the use of centrifugal forces. Efficient removal of interfering particles is achieved in this way, together, with long service lives and a minimum of emission.

8 Claims, 1 Drawing Sheet

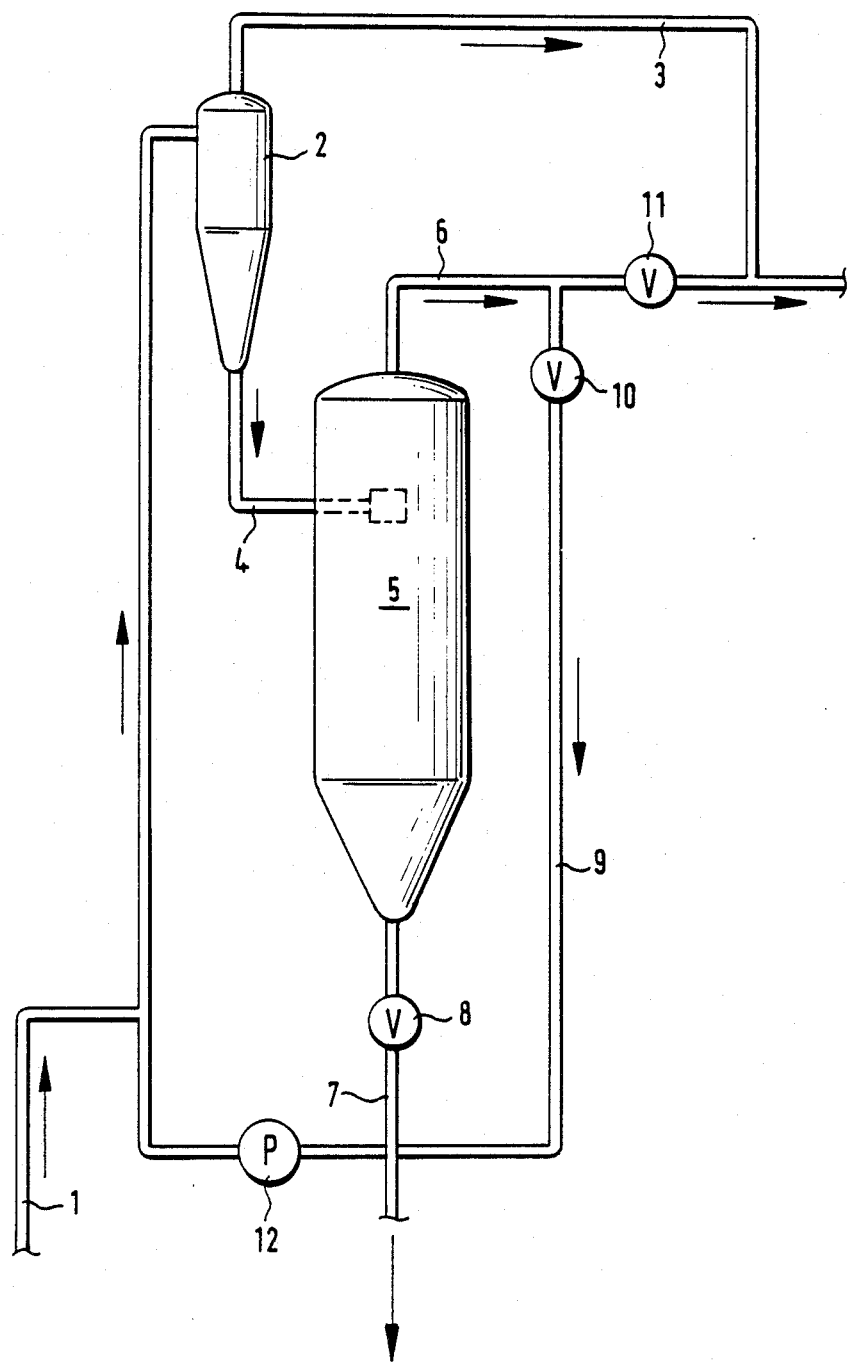

PROCESS AND APPARATUS FOR THE REMOVAL OF SOLID PARTICLES FROM LIQUID CHLORINATED HYDROCARBONS

The invention relates to a process and an apparatus for the removal of solid particles from a mixture containing at least one liquid chlorinated hydrocarbon as defined in claim 1.

When chlorinated hydrocarbons are prepared, particularly when they are vaporized under elevated pressure, and also when vaporized chlorinated hydrocarbons are subjected to thermal cracking and subsequent cooling, undesirable solids, in most cases containing a great deal of carbon, are formed as the result of side reactions. These solids are frequently present in liquid chlorinated hydrocarbons or mixtures thereof which, for example, are a residue from evaporation or are formed by condensation. These solids result in interruptions in production, for example as the result of clogging up or restriction of cross-section and also as the result of poor heat transfer. In such cases, the plant has to be shut down and cleaned, which result in appreciable losses of production and in undesirable emission. It was therefore required to free such liquid chlorinated hydrocarbons or mixtures thereof from solid particles as extensively as possible, so that as little emission as possible should take place.

It is known to use for this purpose, for example, strainer basket filters, but these have to be cleaned frequently, in a tedious manner and with considerable emission, because they rapidly clog up. An improvement is provided by the process described in German Pat. No. 3,219,352, in which an edge filter equipped with a downstream separator is employed instead of the strainer basket filter.

Disadvantages which remain are the relatively high pressure drop in the filter and also a unreliability, inter alia because of moving mechanical parts, which makes it necessary to open the equipment in order to eliminate the problem, in the course of which emission takes place. Emission of this kind can also arise at the comparatively high pressures in the filter where the shaft is carried through the casing of the equipment. Moreover, agglomeration of solids can take place in strainer basket filters, and this increases the risk of clogging up.

A process has now been found which does not exhibit the disadvantages described above. The new process for the removal of solid particles from a mixture containing at least one liquid chlorinated hydrocarbon comprises passing the liquid mixture containing solids into at least one hydrocyclone equipped with a downstream separator.

The solids-containing liquid mixture should not contain more than 2% by weight of solids, relative to this mixture, since at higher solids contents the process according to the invention can, in general, no longer be carried out in a problem-free manner. There is no lower limit to the solids content of the liquid; in general the solids content will not fall below 0.0001% by weight, relative to the solids-containing liquid mixture, since at such low contents the process according to the invention no longer exhibits any substantial advantages compared with other known processes (for example filters). The liquid mixture containing solids preferably contains 0.0005 to 0.5% by weight of solids, relative to this mixture.

The particle size of the solid can vary within wide limits. The solid should advantageously have a weight average particle size of 50 to 2,000 $\mu$m. Although the process according to the invention can be used for solids having an average particle size above 2,000 $\mu$m, here too it is possible to use other known processes, for example removal bymeans of a coarse-mesh screen. The process according to the invention can also be used below a weight average particle size of 50 $\mu$m, but, in general, there is often no need to remove solids having such a small particle size. Particularly good results are obtained if the mixture employed has solid particles of a weight average particle size of 150 to 1,000 $\mu$m.

The process according to the invention can be carried out within a wide temperature range, which depends, inter alia, on the process parameters selected, which are used, for example, for vaporization of for thermal cracking or even condensation of the chlorinated hydrocarbons. It is preferable to carry out the process at 10° to 270° C., especially at 50° to 160° C.

What has been said concerning the temperature in the preceding paragraph applies analogously to the pressure. Very high pressures will be avoided for purely economic reasons, since they would require the use of unnecessarily expensive equipment. The new process is preferably carried out under a pressure of 1 to 40 bar, especially 8 to 25 bar.

The solid particles can be present in the mixture together with one or more liquid chlorinated hydrocarbons. "Liquid" means liquid under the selected operating conditions of temperature and pressure. The chlorinated hydrocarbons can be saturated, unsaturated, branched and cyclic, and they can contain from 1 to 6 carbon atoms and from 1 to 5 chlorine atoms. It is preferable to use the process according to the invention for solids-containing liquid mixtures containing a predominant proportion of at least one chlorinated hydrocarbon having 2 carbon atoms. For reasons of special industrial importance the process according to the invention is used especially for solids-containing liquid mixtures composed of at least 25% by weight, relative to the mixture, of 1,2-dichloroethane. In addition to the chlorinated hydrocarbons, the liquid mixture can also contain small amounts, in general not more than 1% by weight, relative to the mixture, of other organic compounds, for example non-chlorinated hydrocarbons and compounds which, in addition to carbon, hydrogen and chlorine, also contain oxygen atoms.

In accordance with the invention, the solids-containing liquid mixture is passed into at least one hydrocyclone equipped with a downstream separator. The hydrocyclone can be of various designs. It can, for example, be constructed with its lower end tapering conically or it can be constructed in the form of a cylinder. The solids-containing liquid mixture should advantageously flow in a circle with a maximum radius of 1 to 50 cm in the hydrocyclone. Although radii of circular flow above and below these values are also possible, in general the results achieved with these are not so good. In particular, the solids-containing liquid mixture should flow in a circle having a maximum radius of 5 to 30 cm.

It has proved advantageous for the purposes of the invention for the operating parameters selected to be such that the quotient of the square of the velocity at which the solids-containing liquid mixture flows into the hydrocyclone to the maximum radius of the circle in which the solids-containing liquid mixture flows in the hydrocycle ranges from 50 to 2,000 m/s², in particular from 100 to 1,500 m/s².

The slenderness ratio of the hydrocyclone can vary within considerable limits; it is advantageous for the ratio of the distance between the inlet for the solids-containing liquid mixture in the upper part of the hydrocyclone and the outlet for the liquid mixture enriched in solids at the lower end of the hydrocyclone to the maximum radius of the circle in which the solids-containing liquid mixture flows in the hydrocyclone to be 3 to 30, in particular 5 to 20.

In order to improve the separation effect, it is possible to range at least 2 hydrocyclones in series, just as it is also possible, in order to deal with a larger volume of liquid, to arrange 2 or more hydrocyclones to run in parallel. In such cases, it is frequently unnecessary for each hydrocyclone to have its own separator downstream; the outflow from several hydrocyclones can be led into one separator.

The proportion, relative to the solids-containing liquid mixture fed in, of the high-solids liquid mixture removed from the hydrocyclone depends on the solids content of the liquid fed in, the average particle size of the solid and the difference in density between the solid and liquid constituents. In general, this proportion can be kept smaller at a greater average particle size and a greater difference in density between the solid and liquid constituents. Good results are frequently obtained if the proportion, relative to the solids-containing liquid mixture fed to the hydrocyclone, of the liquid mixture enriched in solids is 0.1 to 10% by weight, preferably 0.5 to 5% by weight.

The liquid which has been substantially freed from solids is drawn off from the upper part of the hydrocyclone and is processed further by known processes. If the separating effect in the first hydrocycle should not have been sufficient, a further hydrocyclone can be interposed here. If only small, but nevertheless interfering, amounts of a very finely particulate solid are present, these can also be removed via a conventional filter, which can then be left on stream for a long time.

The liquid mixture which has been enriched in solids is discharged in the lower part of the cyclone and is fed to a downstream separator either continuously or batchwise. The enriched liquid mixture is preferably subjected to sedimentation of the solid particles, for example in a sedimentation vessel, without the use of centrifugal forces. The solid, which still contains some liquid, is discharged continuously or batchwise in the lower part of the sedimentation vessel and, if appropriate, after volatile constituents have been expelled, is disposed of, for example by burning.

The liquid which has been substantially freed from solids and has been drawn off in the upper part of the sedimentation vessel can, depending on its quality, either be combined with the liquid drawn off above from the hydrocyclone, processed, or can be recycled to the hydrocyclone; a further treatment in a second hydrocyclone is also possible. Examples of suitable sedimentation vessels are simple settling vessels, advantageously those having a conically tapering base and also thickeners.

In a further preferred embodiment of the process according to the invention, at least a fraction of the liquid constituents are evaporated from the liquid mixture which has been enriched in solids and is drawn off from the hydrocyclone. In this case the separator downstream of the hydrocyclone is an evaporator. The stream of vapor evolved from this separator can, for example, be fed to a distillation column.

In principle, suitable separators are also those operating by means of centrifugal forces, such as decanters or (skimmer) centrifuges. As a rule, however, these are not necessary and are also not very advantageous because of their high cost.

FIG. 1 SHOWS THE BEST MODE OF THE INVENTION

The invention also relates to an apparatus for carrying out the process, according to the invention, described earlier in the text, such as is illustrated, for example, in FIG. 1, comprising a hydrocyclone (2) having an inlet (1), an outlet in the upper part (3) and an outlet in the lower part (4) which leads into a vertical cyclindrical vessel (5) having a conically tapering lower section and which ends there, near to the cylinder axis, at least 20% of the total internal height of the vessel (5) below the upper part of this vessel, an outlet (6) in the upper part of the vessel (5) which unites with the outlet (3) from the hydrocyclone (2), and an outlet (7) in the lower part of the vessel (5), which contains an shut-off device (8).

The apparatus according to the invention advantageously contains in addition a line (9) which has an shut-off device (10) and a pump (12) and which connects the outlet (6) to the inlet (1) and which branches off from the outlet (6) between the vessel (5) and the junction with the outlet (3), and also an shut-off device (11) in the outlet (6) between the point where the line (9) branches off and the junction with the outlet (3). It is advantageous for the ratio of the total internal height to the internal diameter of the vessel (5) to be 3 to 10.

The process according to the invention and the apparatus according to the invention make it possible to remove solid particles from a mixture containing at least one liquid chlorinated hydrocarbon to such an extent that the purified liquid can be used without difficulty in the further procedure. The process can be operated continuoustly in apparatus which, with the exception of the pump (12), which is not required in every case, does not contain any continuously moving mechanical parts. Long service life and a minimum of emission are achieved.

The following examples are intended to illustrate the invention in greater detail:

EXAMPLE 1

An apparatus according to FIG. 1 is used. 10,000 kg/hour of a solids-containing liquid mixture which is composed of 96% by weight, relative to the total mixture, of a mixture of 1,2-dichloroethane and vinyl chloride and which contains 0.0018% by weight, relative to the total mixture, of solids having a weight average particle size of 810 $\mu$m, are introduced via the line (1), at a temperature of 80° C., under a pressure of 1.6 MPa and at an inlet flow velocity of 4.6 m/s, into the upper section of a hydrocyclone (2). In the hydrocyclone (2), the solids-containing liquid mixture flows in a circle of maximum radius 5 cm, and the ratio of the square of the inlet flow velocity to the maximum circle radius is 423 m/s². The outlet aperture in the lower section of the hydrocyclone (2) is located at a distance of 40 cm from the inlet aperture, and the ratio of the distance between the inlet and the lower outlet to the maximum circle radius in the hydrocyclone (2) is 8. 250 kg/hour of a liquid mixture which has been enriched in solids and which contains 0.071% by weight of solids, relative to the total mixture discharged, is drawn off from the lower outlet aperture and is fed via the line (4) to a sedimentation vessel (5) of capacity 1 m³. Thus 2.5% by weight of the liquid mixture containing solids which has been fed in ar drawn off at the base from the hydrocyclone (4).

5 kg/hour of a solid/liquid mixture are drawn off batchwise in the lower part of the sedimentation vessel (5) via the line (7) in portions of 40 kg each and are disposed of. This solid/liquid mixture contains 3.31% by weight of dry solids, relative to the mixture, i.e. 92% by weight of the solids fed into the hydrocyclone (4) together with the liquid mixture containing solids have been removed.

9,750 kg/hour of liquid mixture which has been substantially freed from solids are drawn off at the head of the hydrocyclone (2) via the line (3), and 245 kg/hour of liquid mixture which has been substantially freed from solids are drawn off at the head of the sedimentation vessel (5) via the line (6). The two streams of liquid are jointly worked up further by distillation in a column. The distillation column runs for about 2.5 times as long as it would without the removal of solids by the process according to the invention.

EXAMPLE 2

An apparatus according to FIG. 1 is used. 17,500 kg/hour of a solids-containing liquid mixture which is composed of 97.5% by weight, relative to the total mixture, of a mixture of 1,2-dichloroethane and vinyl chloride and which contains 0.0025% by weight, relative to the total mixture, of solids having a weight average particle size of 970 μm, are introduced via the line (1), at a temperature of 95° C., under a pressure of 1.6 MPa and at an inlet flow velocity of 8.3 m/s, into the upper part of a hydrocyclone (2). In the hydrocyclone (2), the solids-containing liquid mixture flows in a circle having a maximum radius of 5 cm, the ratio of the square of the inlet flow velocity to the maximum circle radius being 1,380 m/s². The outlet aperture in the lower part of the hydrocyclone (2) is located at a distance of 40 cm from the inlet aperture, and the ratio of the distance between the inlet and the lower outlet to the maximum circle radius in the hydrocyclone (2) is 8. 500 kg/hour of a liquid mixture which has been enriched in solids and which contains 0.092% by weight of solids, relative to the total mixture discharged, is drawn off from the internal outlet aperture and is fed via the line (4) to a sedimentation vessel (5) of capacity 1 m³. Thus 2.86% by weight of the solids-containing liquid mixture fed in are drawn off at the base from the hydrocyclone (4).

15 kg/hour of a pasty solid/liquid mixture are drawn off continuously—batchwise, in portions of 45 kg— each in the lower part of the sedimentation vessel (5) via the line (7) and are disposed of. This solid/liquid mixture contains 2.81% by weight, relative to the mixture, of dry solids, i.e. 96.3% by weight of the solids fed via the line (1) into the hydrocyclone (4) together with the solids-containing liquid mixture have been removed.

17,485 kg/hour of liquid mixture which has been substantially freed from solids are drawn off at the heat of the hydrocyclone (2) via the line (3) and 485 kg/hour of liquid mixture which has been substantially freed from solids are drawn off at the head of the sedimentation vessel (5) via the line (6). The stream of liquid removed via the line (3) is worked up further by distillation in a column, and the stream of liquid removed via the line (6) is recycled to the hydrocyclone (2) via the line (9) and the pump (12). The distillation column runs for about 2.8 times as long as it would without the removal of solids by the process according to the invention.

We claim:

1. A process comprising: removing solid particles from a mixture containing at least one liquid chlorinated hydrocarbon, by introducing the solids-containing liquid mixture into at least one hydrocyclone, drawing off from the upper part of the cylone liquid substantially freed from solid particles, discharging from the lower part of the cylone a liquid mixture enriched in solid particles and feeding that mixture directly to a dopwnstream separator.

2. The process as claimed in claim 1, wherein the solids-containing liquid mixture contains not more than 2% by weight of solids, relative to the mixture.

3. The process as claimed in claim 1, wherein the solids-containing liquid mixture in the hydrocyclone flows in a circle having a maximum radius of 1 to 50 cm.

4. A process as claimed in claim 1, wherein the quotient of the square of the inlet flow speed of the solids-containing liquid mixture to the maximum radius of the circle in which the solids-containing liquid mixture flows in the hydrocyclone is 50 to 2,000 m/s².

5. The process as claimed in claim 1, wherein the ratio of the distance between the inlet for the solids-containing liquid mixture in the upper part of the hydrocyclone and the outlet for the liquid mixture enriched in solids at the lower end of the hydrocyclone to the maximum radius of the circle in which the solids-containing liquid mixture flows in the hydrocyclone is 3 to 30.

6. The process as claimed in claim 1, wherein the liquid mixture which has been enriched in solids and is discharged from the hydrocyclone is subjected to sedimentation of the solid particles.

7. The process as claimed in claim 1, wherein at least a fraction of the liquid constituents are evaporated from the liquid mixture which has been enriched in solids and is drawn off from the hydrocyclone.

8. The process as claimed in claim 1, wherein the solids-containing liquid mixture contains predominantly chlorinated hydrocarbons having 2 carbon atoms.

* * * * *